US00PP34295P2

(12) United States Plant Patent
Wood

(10) Patent No.: US PP34,295 P2
(45) Date of Patent: Jun. 7, 2022

(54) ***KOLKWITZIA* PLANT NAMED 'SMNKADTF'**

(50) Latin Name: *Kolkwitzia amabilis*
Varietal Denomination: SMNKADTF

(71) Applicant: Timothy D. Wood, Spring Lake, MI (US)

(72) Inventor: Timothy D. Wood, Spring Lake, MI (US)

(73) Assignee: SPRING MEADOW NURSERY INC., Grand Haven, MI (US)

( * ) Notice: Subject to any disclaimer, the term of this patent is extended or adjusted under 35 U.S.C. 154(b) by 0 days.

(21) Appl. No.: 17/492,629

(22) Filed: Oct. 3, 2021

(51) Int. Cl.
*A01H 5/02* (2018.01)
*A01H 6/00* (2018.01)
*A01H 5/12* (2018.01)

(52) U.S. Cl.
USPC ..... Plt./226
CPC ..... *A01H 6/00* (2018.05); *A01H 5/02* (2013.01); *A01H 5/12* (2013.01)

(58) Field of Classification Search
USPC ..... Plt./226
CPC ..... A01H 6/00
See application file for complete search history.

*Primary Examiner* — Anne Marie Grunberg
(74) *Attorney, Agent, or Firm* — C. Anne Whealy

(57) ABSTRACT

A new and distinct cultivar of *Kolkwitzia* plant named 'SMNKADTF', characterized by its compact, upright to outwardly spreading and uniformly mounding plant habit; vigorous growth habit and rapid growth rate; freely branching habit; dense and bushy appearance; medium green-colored leaves; numerous pale purple-colored flowers with orange yellow-colored throats; and good garden performance.

2 Drawing Sheets

Figure 1:
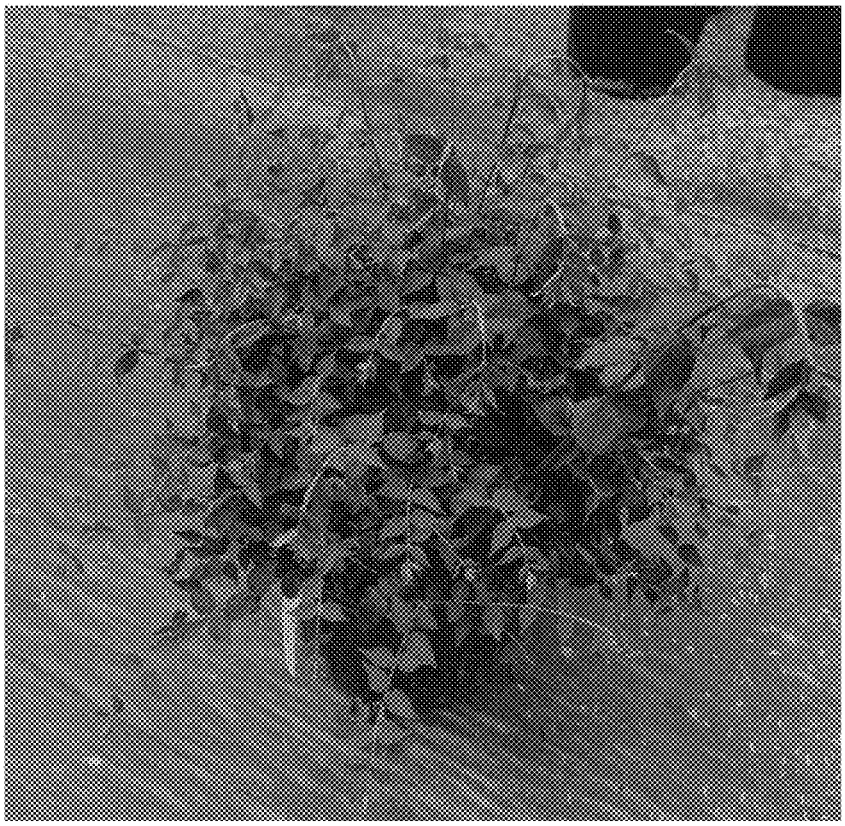

Botanical designation: *Kolkwitzia amabilis.*
Cultivar denomination: 'SMNKADTF'.

STATEMENT REGARDING PRIOR DISCLOSURES BY INVENTOR/APPLICANT & ASSIGNEE

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Kolkwitzia* plant, botanically known as *Kolkwitzia amabilis*, commonly referred to as Beauty Bush and hereinafter referred to by the cultivar name 'SMNKADTF'.

The new *Kolkwitzia* is a product of a planned breeding program conducted by the Inventor in Grand Haven, Mich. The objective of the breeding program was to develop new compact, uniform and freely flowering *Kolkwitzia* plants with attractive leaf and flower coloration.

The new *Kolkwitzia* plant originated from an open-pollination in 2008 in Grand Haven, Mich. of unnamed proprietary selection of *Kolkwitzia amabilis*, not patented, as the female, or seed, parent with an unknown selection of *Kolkwitzia amabilis* as the male, or pollen, parent. The new *Kolkwitzia* plant was discovered and selected by the Inventor in 2013 as a single flowering plant within the progeny of the stated open-pollination in a controlled environment in Grand Haven, Mich.

Asexual reproduction of the new *Kolkwitzia* plant by softwood stem cuttings in a controlled greenhouse environment in Grand Haven, Mich. since 2013 has shown that the unique features of this new *Kolkwitzia* plant are stable and reproduced true to type in successive generations of asexual reproduction.

SUMMARY OF THE INVENTION

Plants of the new *Kolkwitzia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNKADTF'. These characteristics in combination distinguish 'SMNKADTF' as a new and distinct *Kolkwitzia* plant:

1. Compact, upright to outwardly spreading and uniformly mounding plant habit.
2. Vigorous growth habit and rapid growth rate.
3. Freely branching habit; dense and bushy appearance.
4. Medium green-colored leaves.
5. Numerous pale purple-colored flowers with orange yellow-colored throats.
6. Good garden performance.

Plants of the new *Kolkwitzia* can be compared to plants of the female parent selection. In side-by-side comparisons, plants of the new *Kolkwitzia* are more dwarf and more uniformly mounded than plants of the female parent selection.

Plants of the new *Kolkwitzia* can also be compared to plants of *Kolkwitzia amabilis* 'Pink Cloud', not patented. In side-by-side comparisons, plants of the new *Kolkwitzia* differ primarily from plants of 'Pink Cloud' in the following characteristics:

1. Plants of the new *Kolkwitzia* are more dwarf than plants of 'Pink Cloud'.
2. Plants of the new *Kolkwitzia* are more uniformly mounded than plants of 'Pink Cloud'.
3. Plants of the new *Kolkwitzia* are not as freely flowering as plants of 'Pink Cloud'.

BRIEF DESCRIPTION OF THE PHOTOGRAPHS

The accompanying colored photographs illustrate the overall appearance of the new *Kolkwitzia* plant showing the colors as true as it is reasonably possible to obtain in colored reproductions of this type. Colors in the photographs may differ slightly from the color values cited in the detailed botanical description which accurately describe the colors of the new *Kolkwitzia* plant.

The photograph on the first sheet (FIG. 1) is a side perspective view of a typical plant of 'SMNKADTF'.

Figure 2:
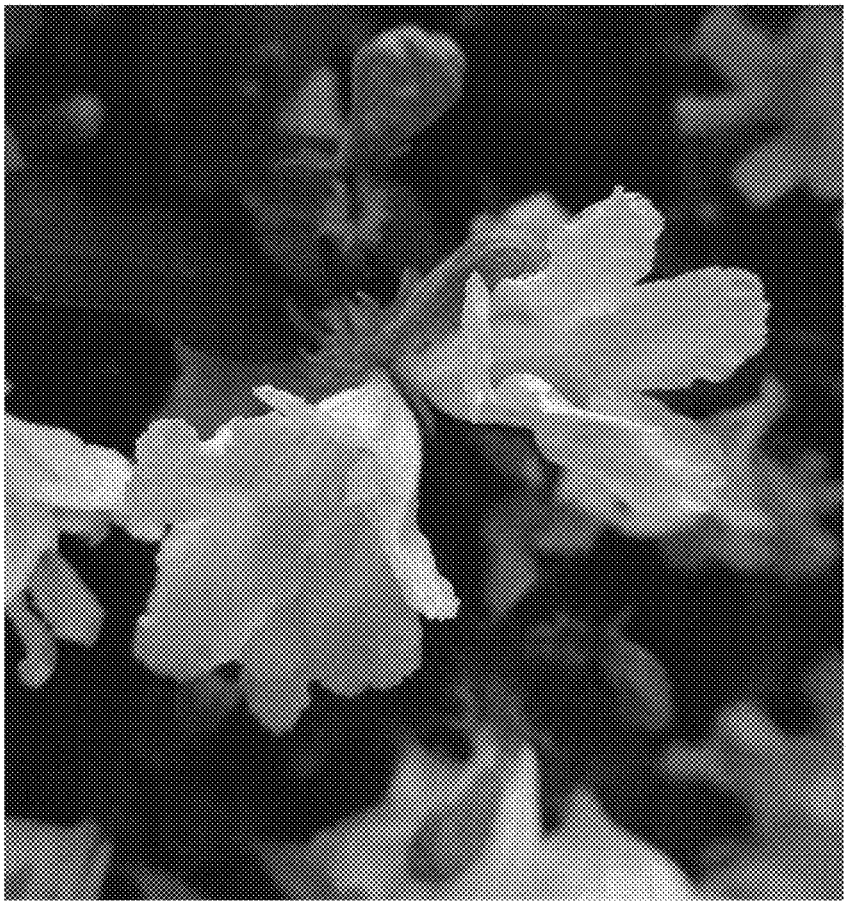

The photograph on the second sheet (FIG. 2) is close-up view of a typical flowering plant of 'SMNKADTF'.

DETAILED BOTANICAL DESCRIPTION

The aforementioned photographs and following observations, measurements and values describe plants grown in the spring and summer in three-gallon containers in a polypropylene-covered shadehouse in Grand Haven, Mich. and under cultural practices typical of commercial *Kolkwitzia* production. During the production of the plants, day temperatures ranged from 18° C. to 27° C. and night temperatures ranged from 5° C. to 10° C. Plants were two years old when the photographs and the description were taken. In the description, color references are made to The Royal Horticultural Society Colour Chart, 2015 Edition, except where general terms of ordinary dictionary significance are used.

Botanical classification: *Kolkwitzia amabilis* 'SMNKADTF'.

Parentage:

*Female, or seed, parent*.—Unnamed proprietary selection of *Kolkwitzia amabilis*, not patented.

*Male, or pollen, parent*.—Unknown selection of *Kolkwitzia amabilis*, not patented.

Propagation:

*Type*.—By softwood stem cuttings.

*Root description*.—Fine; fibrous; typically tan to beige in color, actual color of the roots is dependent on substrate composition, water quality, fertilizer, substrate temperature and physiological age of roots.

*Rooting habit*.—Freely branching; medium density.

Plant description:

*Plant form and growth habit*.—Perennial deciduous shrub; compact, upright to outwardly spreading and uniformly mounding plant habit; vigorous growth habit and rapid growth rate.

*Branching habit*.—Freely branching habit; about 20 to 25 lateral branches develop per plant; pinching enhances lateral branch development.

*Plant height*.—About 37 cm.

*Plant diameter* (*area of spread*).—About 80 cm to 100 cm.

Lateral branch description:

*Length*.—About 40 cm to 50 cm.

*Diameter*.—About 2 mm to 3 mm.

*Internode length*.—About 3 cm.

*Aspect*.—About 20° to 45° from vertical.

*Strength*.—Strong; somewhat flexible.

*Texture*.—Slightly pubescent on youngest stems; with subsequent development, mostly smooth and glabrous.

*Color, developing, upper and lower surfaces*.—Close to 144A tinged with close to 174A.

*Color, developed, lower surface*.—Close to 199D becoming closer to 165A with subsequent development.

Leaf description:

*Arrangement*.—Opposite, simple.

*Length*.—About 2 cm to 4 cm.

*Width*.—About 5 mm to 20 mm.

*Shape*.—Lanceolate.

*Apex*.—Acuminate.

*Base*.—Obtuse.

*Margin*.—Entire.

*Texture, upper and lower surfaces*.—Slightly glabrous.

*Venation pattern*.—Pinnate.

*Color*.—Developing leaves, upper surface: Close to 137B. Developing leaves, lower surface: Close to 146B. Fully expanded leaves, upper surface: Close to NN137B; venation, close to 147B. Fully expanded leaves, lower surface: Close to 147B; venation, close to 147B.

*Petioles*.—Length: About 3 mm. Diameter: About 1 mm. Texture, upper and lower surfaces: Slightly pubescent. Color, upper surface: Close to NN137B. Color, lower surface: Close to 147B.

Flower description:

*Flower appearance and arrangement*.—Single salverform flowers; flowers axillary; freely flowering habit with about 20 to 40 flowers developing per lateral branch with numerous flowers developing per plant during the flowering season; flowers face upright to outwardly.

*Fragrance*.—Slightly fragrant; floral, sweet and pleasant.

*Natural flowering season*.—Plants flower continuously during the spring in Michigan; flowers persistent.

*Flower diameter*.—About 2 cm by 2 cm.

*Flower depth*.—About 2 cm.

*Flower throat diameter* (*at base of petal lobes*).—About 8 mm.

*Flower tube length*.—About 8 mm.

*Flower tube diameter* (*at base of tube*).—About 1 mm.

*Flower buds*.—Length: About 8 mm. Diameter: About 3 mm. Shape: Obovate. Color: Close to 64C and 65D.

*Petals*.—Quantity and arrangement: Five or six in a single whorl. Length: About 5 mm. Width: About 4 mm. Shape: Oblong. Apex: Obtuse, praemorse. Margin: Entire to crenate. Texture, upper and lower surfaces (including throat and tube): Smooth; soft and delicate; glabrous. Color: When opening, upper surface: Close to N75D. When opening, lower surface: Close to N75C. Fully opened, upper and lower surfaces: Close to N75D. Flower tube: Close to N57D. Flower throat: Close to N75D with dense spots, close to 17A.

*Sepals*.—Quantity and arrangement: Five in a single whorl fused at the base and flaring outwardly. Length: About 2 mm. Width: Less than 1 mm. Shape: Acicular. Apex: Acute. Base: Truncate. Margin: Entire. Texture, upper and lower surfaces: Smooth, glabrous. Color, upper and lower surfaces: Close to N144B.

*Peduncles*.—Length: About 8 mm. Diameter: Less than 1 mm. Aspect: About 45° from vertical. Strength: Strong, flexible. Texture: Smooth; glabrous to slightly pubescent. Color, upper and lower surfaces: Close to N144B tinged with close to 174A.

*Reproductive organs*.—Stamens: Quantity per flower: Five; dorsifixed. Filament length: About 7 mm to 10 mm. Filament color: Close to N155A. Anther length: Less than 1 mm. Anther color: Close to 8D. Pollen amount: Scarce. Pollen color: Close to 8D. Pistils: Quantity per flower: One. Pistil length: About 1 cm. Stigma shape: Round. Stigma color: Close to NN155A. Style length: About 1 cm. Style color: Close to NN155A. Ovary color: Close to NN155A.

*Fruits and seeds*.—To date, fruit and seed development have not been observed on plants of the new *Kolkwitzia*.

Garden performance: Plants of the new *Kolkwitzia* have been observed to have good garden performance.

Pathogen & pest resistance: To date, plants of the new *Kolkwitzia* have not been shown to be resistant to pathogens and pests common to *Kolkwitzia* plants.

It is claimed:

1. A new and distinct *Kolkwitzia* plant named 'SMNKADTF' as illustrated and described.

* * * * *